United States Patent [19]
Srisathapat et al.

[11] Patent Number: 5,176,644
[45] Date of Patent: * Jan. 5, 1993

[54] MEDICATION INFUSION PUMP WITH IMPROVED LIQUID-VAPOR PRESSURE RESERVOIR

[75] Inventors: Chad Srisathapat, Sun Valley; Peter C. Lord, Valencia, both of Calif.

[73] Assignee: Minimed Technologies, Ltd., Sylmar, Calif.

[*] Notice: The portion of the term of this patent subsequent to Dec. 1, 2009 has been disclaimed.

[21] Appl. No.: 619,859

[22] Filed: Nov. 29, 1990

[51] Int. Cl.⁵ ............................................. A61M 37/00
[52] U.S. Cl. ............................ 604/141; 128/DIG. 12
[58] Field of Search ............... 604/93, 131, 141, 145, 604/151, 890.1, 891.1, 892.1; 128/DIG. 12

[56] References Cited

U.S. PATENT DOCUMENTS

| | | | |
|---|---|---|---|
| 3,840,009 | 10/1974 | Michaels et al. | 604/892.1 |
| 3,951,147 | 4/1976 | Tucker et al. | 604/891.1 |
| 4,525,164 | 6/1985 | Loeb et al. | 604/131 |
| 4,525,165 | 6/1985 | Fischell | 604/891.1 |
| 4,552,561 | 11/1985 | Eckenhoff et al. | 604/892.1 |
| 4,573,994 | 3/1986 | Fischell et al. | 604/891.1 |
| 4,581,018 | 4/1986 | Jassawalla et al. | 604/891.1 |
| 4,619,653 | 10/1986 | Fischell | 128/DIG. 13 |
| 4,626,244 | 12/1986 | Reinicke | 604/141 |
| 4,655,765 | 4/1987 | Swift | 604/891.1 |
| 4,871,351 | 10/1989 | Feingold | 604/93 |

FOREIGN PATENT DOCUMENTS 0202696 11/1986 European Pat. Off. .......... 604/890.1

Primary Examiner—Gene Mancene
Assistant Examiner—Frank A. LaViola
Attorney, Agent, or Firm—Stuart O. Lowry; Leslie S. Miller

[57] ABSTRACT

An implantable medication infusion pump is provided which utilizes an improved and simplified pressure reservoir to maintain a selected medication in liquid form within a pump housing under a substantially constant pressure. The pressure reservoir comprises a hollow structural enclosure having at least one flexible resilient wall and is adapted to be filled with a selected quantity of a pressure fluid, such as a selected fluorocarbon in a liquid-vapor state, prior to mounting of the reservoir as a structural unit into the infusion pump housing. Within the pump housing, the flexible reservoir wall defines one side of a medication chamber, with the pressure fluid undergoing appropriate change of state to expand or contract the reservoir in a manner maintaining the medication under a substantially constant pressure. The improved reservoir can be provided in a variety of structural shapes and/or utilized in pump housings of various size and shape to permit the pump size to be reduced, or, in the alternative, to increase pump medication capacity without increasing pump housing size.

29 Claims, 2 Drawing Sheets

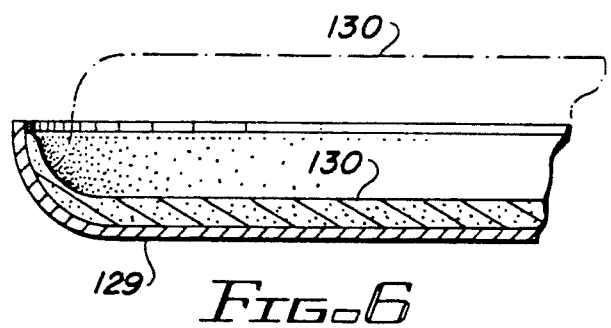
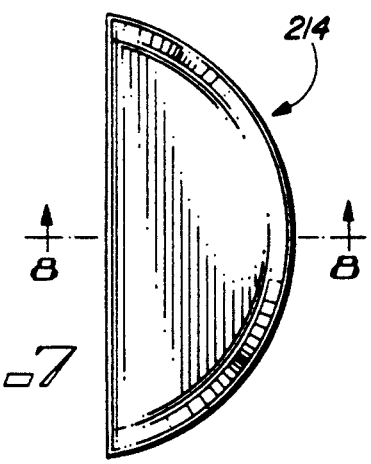
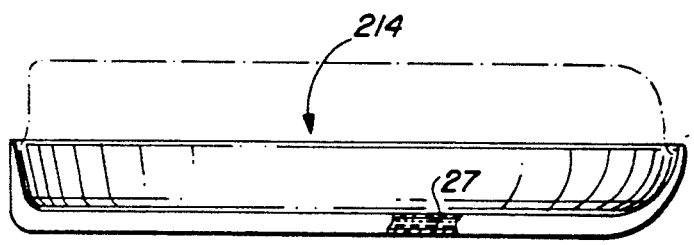
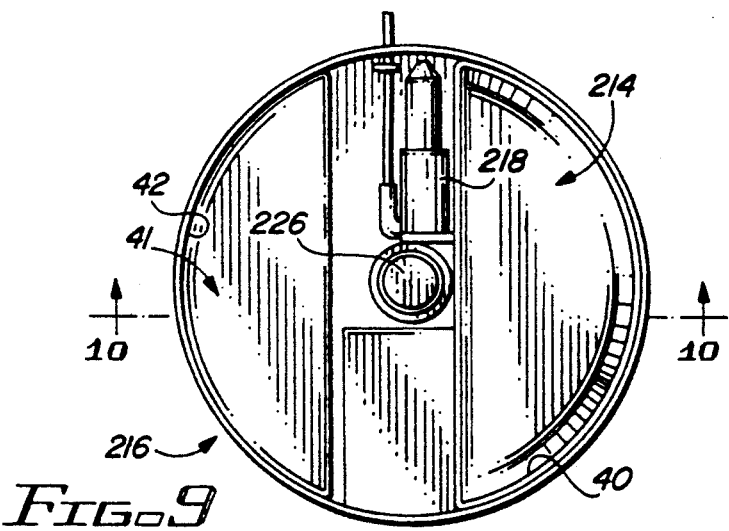
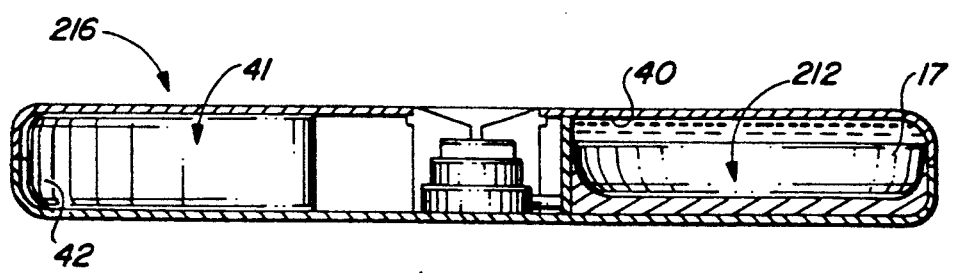

MEDICATION INFUSION PUMP WITH IMPROVED LIQUID-VAPOR PRESSURE RESERVOIR

IDENTIFICATION OF RELATED PATENT APPLICATION

This application is related to another concurrently filed copending patent application, namely U.S. Ser. No. 619,650, entitled "Improved Liquid-Vapor Pressure Reservoir for Medication Infusion Pump."

BACKGROUND OF THE INVENTION

Field of the Invention

This invention relates generally to medication infusion pumps of the type for implantation directly into the body of a patient and for programmed operation to deliver medication to the patient, and more particularly to an improved implantable infusion pump having an improved and simplified fluid pressure reservoir for maintaining a supply of a selected medication under controlled pressure conditions.

Medication infusion pumps are generally known in the art for use in delivering a selected medication to a patient in a scheduled or preprogrammed manner. In recent years, such infusion pumps have been developed in compact form adapted for direct implantation into the body of a patient, to deliver a specific medication such as insulin to the patient in discrete doses over an extended time period. An implanted infusion pump of this general type includes an internal medication chamber for receiving and storing a supply of the selected medication in liquid form, with the medication being subjected to a predetermined storage pressure to ensure accurate and repeatable delivery conditions through the use of a miniature pump and associated programmed control means. In many cases, the storage pressure is maintained at less than ambient body pressure to prevent undesired leakage of the medication from the medication chamber into the body of the patient, and to thereby positively prevent accidental overdose during certain failure modes. For one illustrative example of an implanted medication infusion pump of this general type, see U.S. Pat. No. 4,573,994, to Fischell.

In the past, the medication within the pump medication chamber has been subjected to the desired storage pressure by forming at least a portion of the medication chamber as a movable wall shared with a pressure reservoir charged with a pressure fluid. More particularly, the pressure fluid has comprised a selected fluid in a liquid-vapor state, such as a selected fluorocarbon, wherein the pressure fluid undergoes liquid-vapor change of state at normal body temperature to appropriately expand or contract the pressure reservoir in a manner acting through the movable wall to maintain the medication chamber under substantially constant pressure conditions.

As the medication chamber is filled, the pressure fluid undergoes significant state change to the liquid phase to reduce the volumetric size of the pressure reservoir. Conversely, as the medication is delivered in doses to the patient, the pressure fluid progressively undergoes state change to the vapor phase to maintain the medication under substantially constant pressure. Freon 113 has been used to maintain the medication at a slight negative or subambient pressure in response to normal patient body temperature and altitudinal variations up to about 8,500 feet above sea level.

While such implantable infusion pumps constitute a major step forward in reliable and convenient administration of certain medications, some design aspects of such pumps have contributed to a relatively complex and costly pump construction. For example, the movable wall or barrier separating the pressure reservoir from the medication chamber has been constructed from a metal material to permit leak-free attachment to the pump housing which has also been constructed from a biocompatible metal material, particularly such as titanium or titanium alloy.

Efforts to utilize structurally simple metal foil diaphragms have proven unsatisfactory due to fatigue failures encountered as such diaphragms are displaced during filling and subsequent normal pump operation. Instead, current implantable pumps have utilized metal bellows devices formed from annular metal rings which are interconnected by a series of thin circular welds requiring an extremely high degree of precision and costly manufacturing equipment. Moreover, in use, such metal bellows structures have encountered occasional and highly undesirable fatigue failures. Further, the bellows devices tend to occupy a substantial portion of the internal pump housing volume, resulting in significant limitations in medication capacity or otherwise resulting in a pump housing of relatively large size.

There exists, therefore, a significant need for further improvements in and to implantable medication infusion pumps, particularly with respect to improvements in the design and operational reliability of the movable wall or barrier separating the medication from a liquid-vapor pressure fluid within a pressure reservoir. The present invention fulfills these needs and provides further related advantages.

SUMMARY OF THE INVENTION

In accordance with the invention, a medication infusion pump adapted for implantation into the body of a patient is provided with an improved and simplified yet highly reliable pressure reservoir for maintaining a selected medication under substantially constant pressure conditions. The pressure reservoir is formed as a hollow structural enclosure adapted to be filled or charged with a selected pressure fluid prior to reservoir mounting as a structural unit into the housing of the infusion pump. At least a portion of the pressure reservoir comprises a flexible and resilient wall shared with a medication chamber within the pump housing. The pressure fluid is selected to provide a liquid-vapor state at normal patient body temperature and within a normal altitude range, such that the reservoir expands and contracts as the medication chamber is respectively emptied or filled to subject medication within the medication chamber to substantially constant pressure conditions.

In a preferred form, the pressure reservoir comprises a sack or bag having an appropriate disk-shaped or other suitable configuration for mounting to or into the infusion pump housing. The reservoir bag in constructed from a flexible, impermeable, medication and pressure fluid compatible material. In the preferred embodiment, Halar film is chosen for its compatibility with and relative impermeability to a fluorocarbon pressure fluid such as Freon 113 as well as to medications. The reservoir bag is filled with a selected quantity of the pressure fluid and then appropriately sealed for subsequent mounting as a unit into the pump housing.

Adhesive means or other suitable structural means may be provided within the pump housing to hold the reservoir bag in place and/or to prevent the reservoir bag from obstructing medication flow to a discharge pump for administration to the patient.

In another preferred form, the pressure reservoir can be defined by a relatively rigid plastic base disk adapted for connection to a flexible diaphragm to receive and store the pressure fluid. Once again, Halar film or similar material is preferred for both the base disk and diaphragm. The base disk is adapted for secure and fixed mounting to or within the pump housing, such as by use of an adhesive or the like. The thus-constructed reservoir is adapted for filling with the pressure fluid prior to installation as a unit to or into the pump housing.

In still another preferred form, the pressure reservoir is constructed as a flexible sack or bag to have a generally semicircular shape to receive and store the pressure fluid. The filled bag is adapted for mounting into a pump housing with one side of the bag cooperating with the housing to define a similarly shaped medication chamber. With this geometry, the pressure reservoir and medication can be located at one side of a relatively thin disk-shaped pump housing, with a miniature pump and associated control means located in an opposite semicircular side of the pump housing.

Other features and advantages of the present invention will become more apparent from the following detailed description, taken in conjunction with the accompanying drawings which illustrate, by way of example, the principles of the invention.

DESCRIPTION OF THE DRAWINGS

These and other advantages of the present invention are best understood with reference to the drawings, in which:

FIG. 6 is an enlarged fragmented vertical sectional view of a portion of the pressure reservoir of FIG. 4 and illustrating operation of the reservoir during pump operation to deliver medication to a patient;

FIG. 7 is a top plan view of another alternative preferred form of the liquid-vapor pressure reservoir of the present invention;

FIG. 8 is an enlarged transverse vertical sectional view taken generally on the line 8—8 of FIG. 7;

FIG. 9 is a top plan view of an implantable infusion pump adapted for use with the pressure reservoir of FIGS. 7 and 8, with an upper portion of the pump housing removed to illustrate the arrangement of pump components; and FIG. 10 is an enlarged vertical sectional view taken generally on the line 10—10 of FIG. 9.

DETAILED DESCRIPTION OF THE PREFERRED EMBODIMENT

Figure 1:
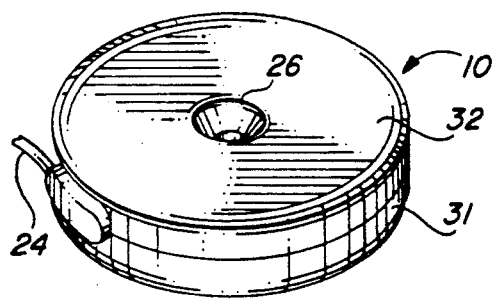
FIG. 1 is a perspective view of an implantable medication infusion pump adapted for implantation into the body of a patient, and further adapted to include a simplified liquid-vapor pressure reservoir embodying the novel features of the invention.
Figure 2:
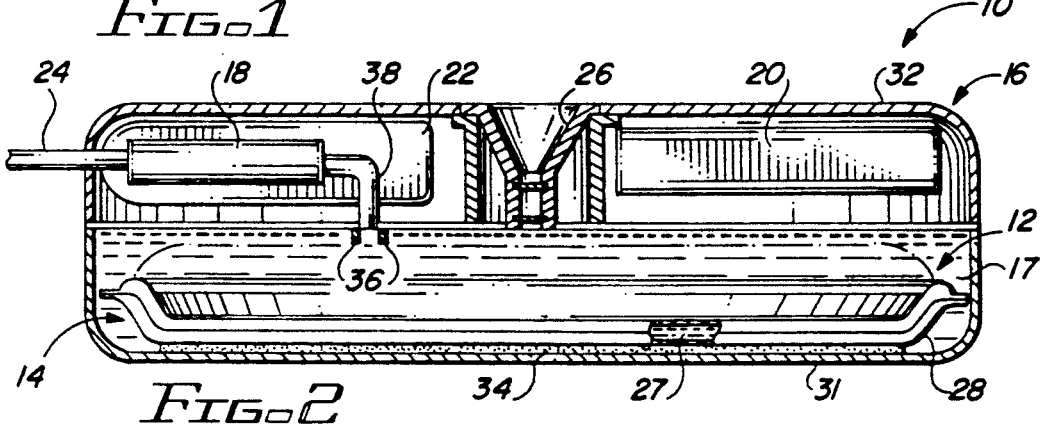
FIG. 2 is an enlarged vertical sectional view of the pump of FIG. 1, and illustrating the improved and simplified liquid-vapor pressure reservoir.

As shown in the exemplary drawings, an implantable medication infusion pump referred to generally in FIGS. 1 and 2 by the reference numeral 10 is provided for use in administering a selected medication to a patient in a controlled, preprogrammed manner. The infusion pump 10 receives and stores a quantity of the selected medication within an internal medication chamber 12 (FIG. 2), wherein the medication is subjected to a predetermined and substantially constant pressure through the use of an improved and simplified pressure reservoir 14.

The illustrative medication infusion pump 10 comprises a small and substantially self-contained unit for direct implantation into the body of a patient. The pump 10 comprises a hermetically sealed pump housing 16 made from a biocompatible material such as titanium or titanium alloy. The pump housing 16 defines the internal medication chamber 12 for receiving and storing the supply of the selected medication 17 in liquid form, such as insulin for a diabetic patient. The pump housing 16 further encases a miniature dispensing pump 18 and associated electronic control circuitry 20 in combination with a battery 22 for periodically operating the pump 18 to deliver medication doses from the chamber 12 to the patient via an appropriate catheter 24 or the like.

The control circuitry 20 is suitably preprogrammed to deliver the medication in accordance with individual patient need. An inlet or refill fitting 26 on the pump housing 16 is adapted to receive a hypodermic needle (not shown) to permit percutaneous refilling of the medication chamber 12 without requiring surgical access to the infusion pump 10. For a more detailed description of the overall construction and operation of implantable infusion pumps of this general type, see U.S. Pat. Nos. 4,373,527 and 4,573,994, both to Fischell, both of which are hereby incorporated herein by reference.

The infusion pump 10 includes the variable volume pressure reservoir 14 mounted within the pump housing 16 with at least one wall of the pressure reservoir 14 exposed to and thereby defining at least a portion of the medication chamber 12. More particularly, the pressure reservoir 14 contains a selected pressure fluid 27 adapted to vary the volumetric size of the medication chamber 12 in accordance with the quantity of medication therein to maintain the medication under substantially constant pressure conditions. A preferred pressure fluid comprises a fluorocarbon which has a substantially linear pressure characteristic as it changes from liquid to vapor state and vice versa at normal human body temperature and at a normal range of altitudes. A preferred pressure fluid is Freon 113 which assumes a liquid-vapor state at normal body temperature and at altitude variations up to about 8,500 feet above sea level to exert a slightly negative and substantially constant pressure of approximately −2.5 to −4.0 psi on the medication chamber 12.

This slight negative pressure beneficially confines the medication against undesired leakage from the pump housing 16 into the body of the patient in the event of a crack or other damage to the pump housing 16. Alternately, other liquid-vapor pressure fluids are known in the art for applying other specific pressures to the medication, such as a positive pressure as may be required for some implantable pump designs. Such an application will be discussed below.

In any event, in accordance with primary aspects of the present invention, the pressure reservoir 14 has a simplified and improved construction for achieving significant reductions in the pump complexity and cost, as well as significant improvements in pump reliability. In addition, the improved pressure reservoir provided by the present invention permits the implantable pump 10 to have an increased medication-containing capacity without increasing pump size, or alternately to have a decreased overall size without reducing pump medication-containing capacity.

Figure 3:
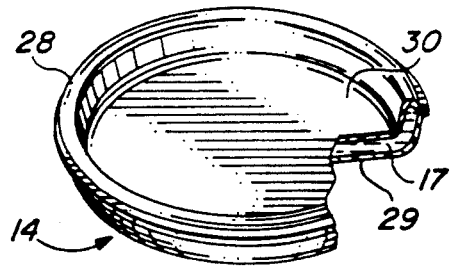
FIG. 3 is a fragmented perspective view depicting a preferred liquid-vapor pressure reservoir construction.

More specifically, with reference to FIGS. 2 and 3, the pressure reservoir 14 comprises a flexible and expansible sack or bag 28 shown with a generally disk-shaped configuration and defined by circular sheets 29 and 30 of plastic film material connected about their peripheries by heat sealing or the like to form a hollow interior. This flexible bag 28 is formed as a structural unit separate from the remaining components of the infusion pump 10, and is desirably filled with the pressure fluid 27 prior to mounting of the bag 28 into the pump housing 16.

A preferred material used to construct the bag 28 is ethylene-chlorotrifluoroethylene copolymer (ECTFE), which is sold under the name Halar by Ausimont USA of Morristown, N.J. In this regard, Halar film is especially suited for use in the environment of implantable infusion pumps due to its relatively high compatibility with and impermeability to fluorocarbon pressure fluids, such as Freon 113, as well as to its compatibility with and impermeability to medications.

The thus-constructed pressure reservoir 14 comprises a flexible yet self-contained structural unit adapted for relatively simple and cost-efficient mounting into the pump housing 16, such as by placement into a lower shell-shaped housing half 31 prior to assembly of the lower half 31 with an upper shell-shaped housing half 32 having the pump 18, the circuitry 20 and the battery 22 installed therein. An adhesive 34 may be used to seat and retain the lower sheet 29 of the bag 28 against the lower housing half 31, such that the opposite or upper sheet 30 of the bag defines a movable wall at one side of the medication chamber 12. Short spacer posts 36 may be provided around an intake port 38 leading to the miniature pump 18 to prevent any portion of the bag 28 from obstructing medication flow from the chamber 12 to the pump for administration to the patient.

In operation, the liquid-vapor pressure fluid within the pressure reservoir 14 expands and contracts the reservoir volume in a manner inversely varying the volume of the medication chamber 12. In particular, as the medication chamber 12 is filled with medication, the pressure fluid undergoes appropriate change of state to the liquid phase to the extent necessary to accommodate the medication yet maintain the medication under a substantially constant pressure. As the medication is dispensed to the patient in individual doses, the pressure fluid undergoes gradual state change to the vapor phase with corresponding expansion of the pressure reservoir sufficiently to maintain the remaining medication in the chamber 12 under substantially constant pressure.

Figure 4:
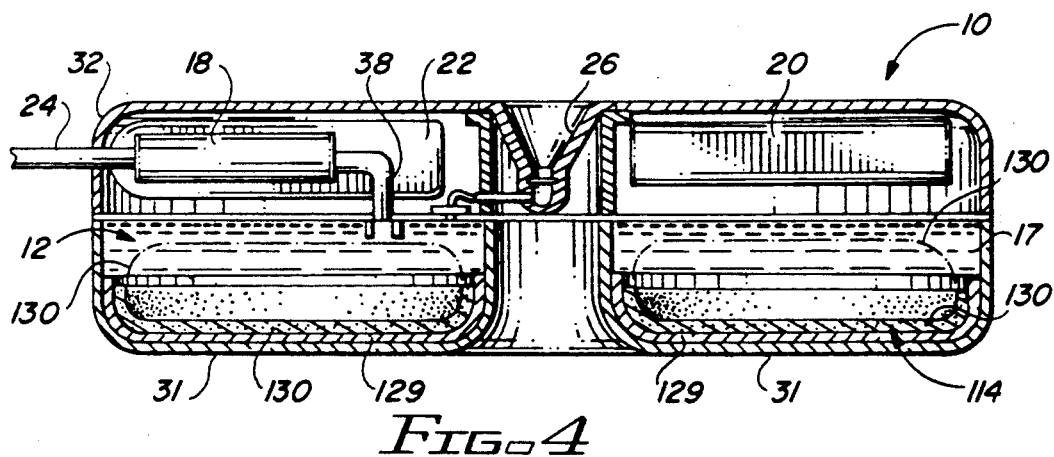
FIG. 4 is an enlarged vertical sectional view similar to FIG. 2, but depicting an implantable infusion pump with a liquid-vapor pressure reservoir of an alternative preferred geometry mounted therein.
Figure 5:
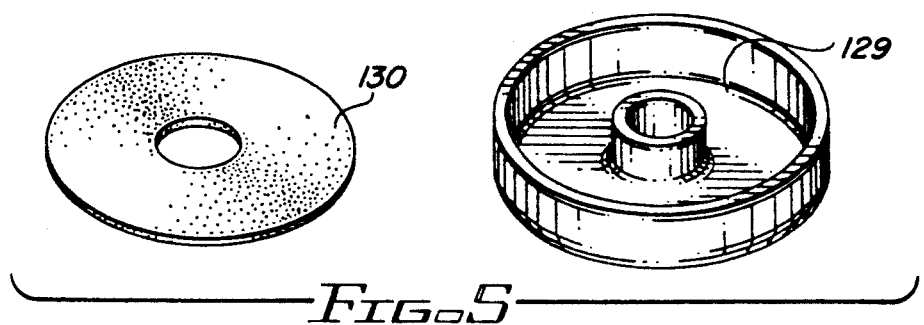
FIG. 5 is an exploded perspective view illustrating assembly of the reservoir depicted in FIG. 4.

An alternative preferred form of the invention is shown in FIGS. 4-6, wherein a modified pressure reservoir 114 is provided to maintain the medication 17 within the infusion pump 10 under substantially constant pressure conditions. In this embodiment, the pressure reservoir 114 is constructed from a relatively more rigid lower base disk 129 formed as by molding to have a generally annular shape and with upturned circular margins at the inner and outer edges thereof. These circular margins are secured by heat sealing or the like to the inner and outer edges of an upper flexible diaphragm 130 of annular shape, wherein the base disk 129 and the diaphragm 130 together define a hollow annular interior for receiving and storing a selected quantity of the pressure fluid 27. Alternately, if desired, the base disk 129 and the attached diaphragm 130 may be formed in a circular or any other selected shape.

The reservoir 114 of FIGS. 4-6 is adapted for filling with the pressure fluid before installation into the pump housing, in generally the same manner and sequence as described with respect to FIGS. 2 and 3. When installed, the base disk 129 can be seated quickly and easily into a lower housing half 31 by means of an adhesive and/or by a mating snap or press fit mounting. The preferred material used to form the base disk 129 and the diaphragm 130 again comprises Halar film or other material having similar properties suitable for use with the selected pressure fluid. In use, the diaphragm 130 is displaced back and forth as the adjacent medication chamber 12 is filled and emptied, as viewed in FIG. 6, such that the medication within the chamber 12 is maintained under substantially constant pressure.

The embodiment of FIGS. 4-6 could easily be varied to exclude the base disk 129, and use the bottom of the lower housing half 31 instead. In this case, the diaphragm 130 would be attached, typically by the use of adhesive, directly to the sides of the lower housing half 31.

FIGS. 7-10 depict another preferred embodiment of the invention, wherein a pressure reservoir 214 is formed as a flexible bag or sack 228 with a generally semicircular shape. In this version of the invention, similarly to the embodiment of FIGS. 2 and 3, the flexible bag 228 is preferably formed from interconnected sheets of Halar film or the like and is adapted to be filled with the selected pressure fluid 27 before installation into a modified pump housing 216. As shown in FIGS. 9 and 10, the flexible bag 228 is mounted as a structural unit into a generally semicircular chamber 40 at one side of the housing 216 which has generally circular disk shape. With this geometry, the pump housing 216 cooperates with one side of the bag 228 to define a semicircular medication chamber 212.

A centrally positioned inlet fitting 226 on the pump housing 216 permits the medication chamber 212 to be filled with the selected medication 17, and a dispensing pump 218 is provided for delivering the medication in doses from the chamber 212 to the patient. The pump 218 is controlled by miniature control circuitry and a battery power source referred to generally in FIGS. 9 and 10 by the reference numeral 41 and positioned in another generally semicircular chamber 42 disposed opposite to the reservoir 214.

The pump configuration shown in FIGS. 9 and 10 thus includes the reservoir 214 and the associated medication chamber 212 in a noncircular shape, in contrast with the traditional circular shape reservoirs and chambers defined in the art through the use of metal bellows devices. Moreover, the reservoir 214 and the medication chamber 212 are generally disposed in a common plane with the other main components of the infusion pump. This arrangement provides a substantial optimization of the available pump housing interior volume and thereby permits the overall pump size to be significantly reduced without sacrificing medication-containing capacity. Alternately, the volumetric capacity of the medication chamber 212 can be significantly increased relative to prior pumps of similar size.

As mentioned above, the flexible bag type pressure reservoir could also be used with a positive pressure pump. Such pumps maintain fluid in a medication chamber at a positive pressure ranging up to, for example, 10 psi. Referring again to FIG. 2, a positive pressure pump could have the medication chamber 12, the pressure reservoir 14, the inlet or refill fitting 26 as shown in FIG. 1.

However, such positive pressure pumps in their simplest form include only a flow restrictor between the reservoir and the catheter. In such a pump, reference numeral 18 in FIG. 1 would refer to a flow restrictor, which is typically a capillary tube. In addition, such simple pumps do not have the circuitry 20 and the battery 22 installed therein.

A slightly more complex positive pressure pump would have a valve (not shown) in series with the flow restrictor, all at reference numeral 18. This type of pump would have the circuitry 20 and the battery 22 installed therein, and could be externally controlled. This type of pump would operate at a fixed flow rate whenever the valve was open.

A still more complex positive pressure pump would use two valves with an accumulator therebetween, as well as the circuitry 20 and the battery 22. This type of pump would be externally controlled by opening first the valve between the medication reservoir and the accumulator to fill the accumulator. This valve would be closed, and the valve between the accumulator and the catheter would be opened to allow the accumulator to pump out the accumulated medication.

Although an exemplary embodiment of the present invention has been shown and described, it will be apparent to those having ordinary skill in the art that a number of changes, modifications, improvements, or alterations to the invention as described herein may be made, none of which depart from the spirit of the present invention. All such changes, modifications, and alterations should therefore be seen as within the scope of the present invention. Accordingly, no limitation on the invention is intended by way of the foregoing description and the accompanying drawings, except as set forth in the appended claims.

What is claimed is:

1. A medication infusion pump, comprising:
   a pump housing having a medication chamber formed therein for receiving a supply of a selected medication;
   pump means within said housing for delivering the medication from said medication chamber to a patient; and
   a pressure reservoir comprising a structural enclosure and having a liquid-vapor pressure fluid therein, said pressure reservoir being defined by a relatively rigid base member connected to a movable diaphragm, said base member being adapted for seated mounting into said pump housing with said diaphragm exposed to said medication chamber, said pressure fluid being adapted to undergo sufficient liquid vapor phase change for varying the volumetric size of said pressure reservoir in response to the quantity of the medication within said medication chamber to maintain the medication under a predetermined and substantially constant pressure, wherein said pressure fluid is selected to maintain the medication chamber under a pressure less than atmospheric pressure.

2. A medication infusion pump as defined in claim 1, wherein said pump housing is hermetically sealed to permit direct implantation into the body of a patent.

3. A medication infusion pump as defined in claim 1, wherein said diaphragm is formed from a flexible, impermeable, medication and pressure fluid compatible material.

4. A medication infusion pump as defined in claim 1, wherein said pressure fluid comprises a selected fluorocarbon, and wherein said base member and said diaphragm are formed from a material having relatively high compatibility with and relatively high impermeability to said fluorocarbon.

5. A medication infusion pump as defined in claim 4, wherein said material is Halar film.

6. A medication infusion pump as defined in claim 1, wherein said base member has a generally annular shape with upturned inner and outer peripheral edges, and wherein said diaphragm has a generally annular shape for added connection to said inner and outer edge of said base member.

7. A medication infusion pump as defined in claim 1, wherein said base member has a size and shape for press fit installation into said pump housing.

8. A medication infusion pump, comprising:
   a pump housing formed from interfitting and generally shell-shaped first and second housing halves;
   pump means mounted within said first housing half, said first and second housing halves when interconnected defining a medication chamber for receiving a supply of a selected medication, said pump means being for delivering the medication from said medication chamber to a patient; and
   a pressure reservoir comprising a structural enclosure having a liquid-vapor pressure fluid therein, said pressure reservoir being defined by a relatively rigid base member having a size and shape for substantially mating seated reception into said second housing half and a movable diaphragm connected to said base member for exposure to said medication chamber when said base member is mounted into said second housing half, said pressure fluid being adapted to undergo sufficient liquid-vapor phase change for varying the volumetric size of said pressure reservoir in response to the quantity of the medication within said medication chamber to maintain the medication under a predetermined and substantially constant pressure, wherein said pressure fluid is selected to maintain the medication chamber under a pressure less than atmospheric pressure.

9. A medication infusion pump as defined in claim 8, wherein said diaphragm is formed from a flexible, impermeable, medication and pressure fluid compatible material.

10. A medication infusion pump as defined in claim 8, wherein said pressure fluid comprises a selected fluorocarbon, and wherein said base member and said diaphragm are formed from a material having relatively high compatibility with and relatively high impermeability to said fluorocarbon.

11. A medication infusion pump as defined in claim 10, wherein said material is Halar film.

12. A medication infusion pump as defined in claim 8, further including electronic control circuitry mounted within said first housing half.

13. A medication infusion pump as defined in claim 12, further including a battery power source mounted within said first housing half.

14. A medication infusion pump, comprising:
a pump housing having a medication chamber formed therein of relatively thin and generally semicircular shape;
pump means within said housing for delivering the medication from said medication chamber to a patient; and
a pressure reservoir comprising a structural enclosure and having a liquid-vapor pressure fluid therein, said pressure reservoir being mounted within said housing and including a movable wall exposed to said medication chamber, said pressure fluid being adapted to undergo sufficient liquid-vapor phase change for varying the volumetric size of said pressure reservoir in response to the quantity of the medication within said medication chamber to maintain the medication under a predetermined and substantially constant pressure, wherein said pressure fluid is selected to maintain the medication chamber under a pressure less than atmospheric pressure.

15. A medication infusion pump as defined in claim 14, wherein said pump housing is hermetically sealed to permit direct implantation into the body of a patent.

16. A medication infusion pump as defined in claim 15, wherein said pressure reservoir comprises an expansible bag.

17. A medication infusion pump as defined in claim 14, wherein said movable wall is formed from a flexible, impermeable, medication and pressure fluid compatible material.

18. A medication infusion pump as defined in claim 14, wherein said pressure fluid comprises a selected fluorocarbon, and wherein said movable wall is formed from a material having relatively high compatibility with and relatively high impermeability to said fluorocarbon.

19. A medication infusion pump as defined in claim 14, wherein said pump means and said medication chamber are disposed generally in a common plane.

20. A medication infusion pump as defined in claim 18, further including electronic control means and a battery power source mounted generally in coplanar relation to said pump means.

21. A medication infusion pump, comprising:
a relatively thin pump housing having a hollow interior and defining a medication chamber within said housing interior for receiving a supply of a selected medication;
pump means within said housing for delivering the medication from said medication chamber to patient; and
a pressure reservoir comprising a structural enclosure of noncircular shape within said medication chamber and defining a movable wall exposed to the medication within said medication chamber, said pressure fluid being adapted to undergo sufficient liquid-vapor phase change for varying the volumetric size of said pressure reservoir in response to the quantity of the medication within said medication chamber to maintain the medication under a predetermined and substantially constant pressure, wherein said pressure fluid is selected to maintain the medication chamber under a pressure less than atmospheric pressure.

22. A medication infusion pump as defined in claim 21, wherein said pump housing is hermetically sealed to permit direct implantation into the body of a patent.

23. A medication infusion pump as defined in claim 21, wherein said pressure reservoir has a generally semicircular shape.

24. A medication infusion pump as defined in claim 23, wherein said medication chamber has a generally semicircular shape.

25. A medication infusion pump as defined in claim 21, wherein said movable wall is formed from a flexible, impermeable, medication and pressure fluid compatible material.

26. A medication infusion pump as defined in claim 21, wherein said pressure fluid comprises a selected fluorocarbon, and wherein said movable wall is formed from a material having relatively high compatibility with and relatively high impermeability to said fluorocarbon.

27. A medication infusion pump as defined in claim 21, wherein said pump means and said medication chamber are disposed generally in a common plane.

28. A medication infusion pump as defined in claim 21, further including electronic control means and a battery power source mounted generally in coplanar relation to said pump means.

29. A medication infusion pump as defined in claim 21, wherein said pressure reservoir comprises an expansible bag.

* * * * *